United States Patent [19]

Moore

[11] Plant 4,619

[45] Jan. 13, 1981

[54] MINIATURE ROSE PLANT

[76] Inventor: Ralph S. Moore, 2519 E. Noble Ave., Visalia, Calif. 93277

[21] Appl. No.: 72,207

[22] Filed: Sep. 4, 1979

[51] Int. Cl.[3] ..... A01H 5/00

[52] U.S. Cl. ..... Plt./9

[58] Field of Search ..... Plt./9

*Primary Examiner*—Robert E. Bagwill
*Assistant Examiner*—James R. Feyrer

[57] ABSTRACT

The subject of this invention is a new and distinct variety of miniature rose plant characterized primarily by its coral pink many petaled flowers and its much branched compact plant with medium green, disease resistant foliage.

1 Drawing Figure

The present invention relates to a new and distinct variety of hardy, dwarf, bush type rose plant of the miniature class; the buds and flowers being, in general color effect, similar to Mary Marshall (miniature — U.S. Plant Pat. No. 3,346).

The variety is further characterized by:

An abundance of bloom, with flowers borne singly or several to the stem in loose clusters.

Light sweet fragrance.

A plant which is vigorous, of rounded upright shape with semi-glossy small foliage with pointed leaflets; the buds and flowers being similar in form and size to Mary Marshall.

The plant, which has a normal height of 12–14 inches or more, can easily be maintained at lesser height by occasional trimming.

A plant which grows and blooms satisfactorily both in greenhouse and outdoors; is good for growing in pots, and provides excellent garden decoration as well as cut flowers.

The present variety of miniature rose was originated by me at Sequoia Nursery, located at Visalia, Calif., under conditions of careful control and observation, as a cross between Little Darling (Floribunda — U.S. Plant Pat. No. 1,581, expired), as the seed parent and New Penny (miniature — not patented) as the pollen parent.

Subsequent to origination of the variety I successfully asexually reproduced it, at Sequoia Nursery, located as aforesaid, by budding as well as by cuttings, the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded to upright; seedling; greenhouse; outdoors; cut flowers; garden decoration; potted plant.

Class: Miniature.

*Variety name.*—Double Joy.

Flowers borne: Singly and several together (3 to 5) on slender wirey stems.

Quantity of bloom: Abundant both outside and in greenhouse.

Bud:

*Peduncle.*—Medium length (20–30 mm — sometimes longer); slender, erect; medium green, sometimes tinted bronze (outdoors); hairs — numerous — very short.

*Before calyx breaks.*—Size — small. Form — pointed with several foliaceous appendages and numerous very short hairs on surface of bud; with foliaceous parts extending beyond the tip of the bud equal to one-half or more of its length. Color — medium green, occasionally tinted with bronze (outdoors).

*As calyx breaks.*—Color — deep pink to red — near Carmine 21/1 with yellowish undertone. May vary from bud to bud depending on exposure to light and temperature. Opening: opens well in all weather.

Bloom: Size when fully open — small, averaging about 35–40 mm.

*Petalage.*—Double, averaging about 70–80 petals, arranged regularly plus sometimes several small petaloids.

*Form.*—Cupped at first, becoming more flat then rounded with full high center and with petals rolled loosely outward; later at maturity outer petals are folded at edge to give a pointed effect and rolled loosely outward and downward. Open flowers may show stamens.

Petals: Fairly thick; satiny on inside and on outside surfaces.

*Shape.*—Outside petals; broad lanceolate (nearly oval) with acute tip; intermediate — broad lanceolate with acute tip; inside — lanceolate with acute tip.

Color: Newly opened flower from a plant grown in plastic greenhouse (August 1979), Visalia, Calif.

*Outside petal.*—Outside surface — near Empire Rose 0621 blending into yellow on basal $\frac{1}{3}$ of petal — becoming near Maize Yellow 607/1 at base. Inside surface — near Empire Rose 0621 blending into near white near base.

*Intermediate petal.*—Outside surface — yellow overlaid with a color near Carmine Rose 621 and blending into yellow at base. Inside surface — color pink — near Coral Pink 0619 blending into yellow at base.

*Inner petal.*—Outside surface — similar to intermediate petal. Inside surface — similar to intermediate petal. Colors noted above can vary according to season of year, light intensity, vigor of plant, etc. General color effect; newly opened flowers — coral pink. Three days open — color similar to newly opened flowers but lighter color (more pink). Behavior — opens well in all weather. Spent petals drop off. Flower longevity (July-August 1979) plant in pot 4-6 days or longer. Cut flowers at living room temperature 4 days or longer.

Reproductive organs:

*Stamens.*—Fairly abundant, arranged regularly about pistils.

*Filaments.*—Varying length, fairly short; yellow.

*Anthers.*—Well formed, yellow.

*Pollen.*—Moderate amount.

*Pistils.*—Average number.

*Styles.*—Fairly even; short; bunched.

*Stigmas.*—Whitish.

*Ovaries.*—All enclosed in calyx.

*Hips.*—Few or several.

*Sepals.*—Permanent; spear shaped, recurved.

*Seed.*—Few or several.

Foliage:

*Leaves.*—Compound of five (sometimes three or seven) leaflets; medium to small; leathery; semi-glossy.

*Leaflets.*—Shape: broad lanceolate, nearly oval; apex acute; base rounded or rounded acute. Margin serrate.

*Color.*—Medium green; new growth — normal (medium) green — sometimes reddish.

*Rachis.*—Medium strength; upper side may have several tiny short hairs, grooved; underside sparsely thorny with few to several tiny hairs.

*Stipules.*—Medium long; narrow to medium width; medium length narrow points which turn out usually at about 45 degrees.

Growth:

*Habit.*—Dwarf; bushy; rounded; upright; much branched.

*Growth.*—Free; vigorous; internodes relatively short.

*Canes.*—Medium; slender; sturdy.

*Main stems.*—Color: medium green.

*Thorns.*—Few to average; slender; straight; color — brown. Prickles — none. Hairs — none.

*Branches.*—Color: medium green. Thorns: few to average; short length; slender; straight. Medium to short oval base. Prickles: none. Hairs: none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, much branched habit, substantially as illustrated and described, characterized by buds and flowers which are coral to rose pink in varying shades and/or blended with yellow, the color resembling Mary Marshall (miniature — U.S. Plant Pat. No. 3,346) with general form and size also resembling Mary Marshall, and further characterized by a plant which is vigorous and compact with abundant medium to small size, semi-glossy, disease resistant foliage, easy to propagate from cuttings and by budding, with an abundance of flowers borne singly or several to the stem in loose clusters.

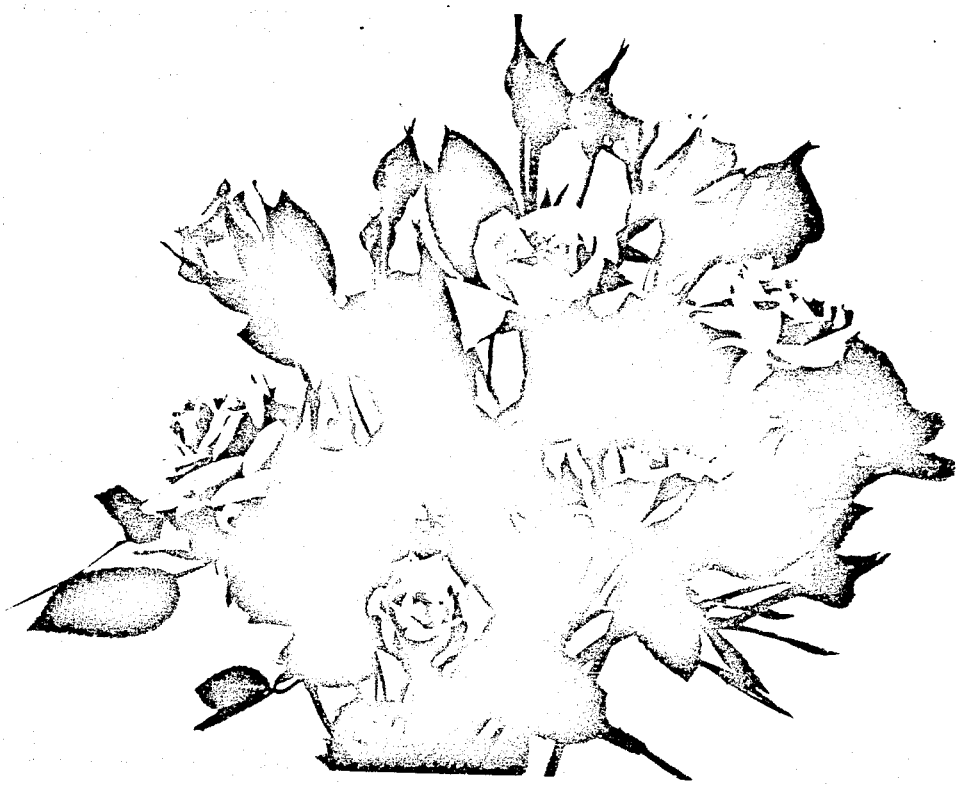

* * * * *